(12) United States Patent
Hu

(10) Patent No.: US 8,263,345 B2
(45) Date of Patent: Sep. 11, 2012

(54) METHOD FOR PREPARING STANDARDIZED SERUM MIXTURE FOR DETERMINING ALLERGEN POTENCY AND THE USE THEREOF

(75) Inventor: Gengxi Hu, Shanghai (CN)

(73) Assignee: Zhejiang Wolwo Bio-Pharmaceutical Co., Ltd., Wukang Town (CN)

( * ) Notice: Subject to any disclaimer, the term of this patent is extended or adjusted under 35 U.S.C. 154(b) by 467 days.

(21) Appl. No.: 12/518,965

(22) PCT Filed: Dec. 14, 2007

(86) PCT No.: PCT/CN2007/071230
§ 371 (c)(1),
(2), (4) Date: Sep. 3, 2009

(87) PCT Pub. No.: WO2008/086721
PCT Pub. Date: Jul. 24, 2008

(65) Prior Publication Data
US 2010/0021946 A1   Jan. 28, 2010

(30) Foreign Application Priority Data
Dec. 14, 2006 (CN) .......................... 2006 1 0147239

(51) Int. Cl.
*G01N 33/53* (2006.01)
(52) U.S. Cl. .......................................... 435/7.1; 435/7.2
(58) Field of Classification Search .................. None
See application file for complete search history.

(56) References Cited

U.S. PATENT DOCUMENTS
6,635,484 B1   10/2003   Laub et al.

FOREIGN PATENT DOCUMENTS
CN   1491723 A   4/2004

OTHER PUBLICATIONS

Akasawa et al. J. Allergy Clin. Immunol. 1996 vol. 97, p. 1116-1120.*
Marchand et al. (Allergy 2003 vol. 58, p. 1037-1043).*
Schou et al. (Clinical & Experimental Allergy 1991 vol. 21, p. 321-328).*
Reid et al., "Underestimation of specific immunoglobulin E by microtiter plate enzyme-linked immunosorbent assays," J. Allergy Clin. Immunol., 1985, vol. 76, No. 2, part 1, pp. 172-176.
International Search Report of PCT/CN2007/071230, dated Mar. 20, 2008.
Yu. "Preparation and calibration of human IgE working standard." Journal of Shanghai Immunology, vol. 7(1), Feb. 1987, pp. 35-37.
Lu. "Determination of allergen specific IgE antibody in the patients with nasal allergy." Journal of Dalian Medical University, vol. 16(2), Mar. 1994, pp. 100-102.

* cited by examiner

*Primary Examiner* — Jacob Cheu
(74) *Attorney, Agent, or Firm* — Hamre, Schumann, Mueller & Larson, P.C.

(57) ABSTRACT

A method for preparing standardized serum mixture for determining allergen potency which comprises: 1) providing multiple serum samples from patients moderately hypersensitive to said allergen; 2) determining the relative content of sIgE against said allergen in each serum sample, obtaining the mean value of the relative content of sIgE of said multiple serum samples, and obtaining deviation value of the relative content of sIgE of each serum with respect to said mean value; 3) removing at least 5% of serum samples that have the largest and smallest deviation values respectively, and mixing the residual sera in the same volume. A serum mixture prepared by the method as well as the use of such serum mixture are also described.

13 Claims, 1 Drawing Sheet

METHOD FOR PREPARING STANDARDIZED SERUM MIXTURE FOR DETERMINING ALLERGEN POTENCY AND THE USE THEREOF

TECHNICAL FIELD

The invention relates to the art of biotechnology medicine, in particularly, to a method for preparing standardized serum mixture for determining allergen potency and the use thereof.

BACKGROUND ART

As the change of ecological environment, people contacts with more and more sensitizing substance, which causes the incidence of allergic disease increasing. At present, approximately 25% of the population in the world is affected by allergic disorder. In 1998, detection of allergen and specific immunotherapy, announced by WHO, is the only etiological treatment which may affect the natural course of hypersensitivity disease and prevent the occurrence of new allergic diseases.

Specific immunotherapy treatment comprises identifying the species of allergen in a patient prior to making the patient contact with preparations containing this species of allergen repeatedly during non-acute stage, and the dosage increases gradually up to the best maintenance dosage so as to enhance the resistance of patients against said species of allergen to control or lessen the symptoms of hypersensitivity. The allergen preparation used refers to a biological product useful for diagnosing, prophylaxis and treatment of hypersensitivity disease. Said allergen preparation is obtained by extracting allergen from containing allergen ingredient natural materials (including insects, mites, fungi, animal danders, pollens, foods, etc), and then preparing a solution having a certain concentration of allergen, or further modifying the preparation by adsorbent or adjuvant.

In the past decades, professionals, organizations and agencies in Europe and America tried to develop an effective method for measuring allergen preparation. Though lots of methods were proposed, none of them had been accepted due to defects. For example, gravimetric volume (W/V) was used to represent the concentration of allergen extract. That is, a certain amount of degreased material (for example 1 g pollen which is degreased) was added into a certain amount (for example, 100 ml) of extraction fluid, then the W/V thereof was 1:100. Although it was very simple, the difference in factors, such as quality of the pollen collected and extraction procedure, may cause the ingredient, content and titer of the product having equivalent W/V value differently. In other words, W/V unit only indicates the concentration of extract, and it has no inevitable relationship with the titer or potency thereof. Additionally, protein nitrogen unit (PNU) was used to normalize the protein content in allergen extract because the main active component in allergen was protein. However, not all the proteins have antigenicity; and there is no definite relationship between the content of protein which has antigenicity and titer (i.e. the gross potency of all the allergic protein), so this method still could not be used to evaluate the gross potency of allergen product accurately. Therefore, WHO considered vaccine product normalized by the above two units as non-standardized product, because the allergen titer can not be compared between products from different manufacturers or different batches.

Biological unit (BU) and bioequivalent allergy unit (BAU) used respectively in Europe and America both are indications reflecting gross potency titer of allergen preparation, which is normalized by the result of direct skin test performed on hypersensitive patients. The BU in Europe was determined based on the dosage of allergen extract which causes the same stripe as histamine dichloride of certain concentration in a pricking test performed on 20 moderately hypersensitive patients, with the test results being represented by geometric mean. BAU was one important reference criteria for producing allergen preparation in US. Intracutaneous test was performed on 15 highly hypersensitive patients, and the titer of allergen was determined based on the arithmetic mean value, among all patients, of the concentrations which cause the patient to have 50 mm erythema in diameter. Both BU and BAU were based on in vivo allergic reaction in patients. That is, detection of IgE antibody in vivo against allergen may evaluate the gross titer more accurately. However, such methods depend on the availability of allergic patients as well as the criteria for selecting patients.

Methods for determining IgE in vitro to detect gross allergen potency include radioallergosorbent inhibitory test (RAST), enzyme linked immunosorbent inhibitory assay (ELISA), which are used to detect major allergen. These methods include radioallergosorbent inhibitory test (RAST-I) and many new in vitro assays developed based on RAST-I, such as MAST, FAST as well as Pharma-CAP, etc. Results of assay depend on the composition of serum pool and allergen extract bound to solid phase carrier, both of which are not reproducible. However, it is still impossible for such methods to standardize allergen preparation, because of the absence of stable serum pool between different batches.

Since allergen preparation is obtained by extraction from natural material, those factors, such as time, place and method for collecting, growth environment and extracting process of raw material, will increase the diversity of the quality of raw material. Moreover, allergens themselves are a complicated mixture of variants, and their epitopes are not entirely identical. Furthermore, immune reaction of individual patient is not the same. At present, methods for determining allergen potency in vitro all involve standardized serum, however, there is great difference between the serum collected each time. Therefore, it is difficult to control the quality of allergen preparation. The key to success of immune therapy lies in the use of high-quality allergen preparation which may be standardized and produced continuously. The purpose for standardization is to reduce the difference in product qualification and quantification, to increase safety, validity, reliability and accuracy, thus improving the diagnosis and treatment of allergic disease. The potency of allergen preparation is an important index for its quality control, since allergen preparation is used in diagnosis and treatment only after determining the potency of the preparation. However, it is impossible to compare products with each other, since the units used to indicate the results are not consistent when determining the potency of allergen.

Therefore, it is urgently desired in the art to provide a standardized serum mixture for detecting the potency of allergen preparation.

DISCLOSURE OF INVENTION

For solving the problems said above, in the first aspect, the invention provides a method for preparing a standardized serum mixture that is used to detect the allergen potency, which comprises the following steps:

1) providing multiple serum samples from multiple patients moderately hypersensitive to said allergen;

2) determining the relative content of said allergen-sIgE in each serum sample, and obtaining the mean value of the relative content of sIgE in said sera as well as the deviation value of the relative content of sIgE in each serum with respect to said mean value;

3) removing at least 5% of the serum samples with the largest and smallest deviation values respectively, and mixing the residual sera in the same volume.

In one preferable embodiment, said moderately hypersensitive patients in said step 1) are patients that produce reaction of grade +++ when performing skin prick test with said allergen.

In a preferable embodiment, the relative content of sIgE in serum is determined by Unicap method in said step 2). The mean value of said relative content of sIgE in serum samples is within the range of 75-85 and the sera with the absolute value of the deviation being less than 30 are mixed at the same volume.

In another preferable embodiment, the relative content of sIgE in serum is determined by ELISA in said step 2). Mean of said relative content of sIgE in serum is within the range of 0.9-1.0 and the sera with the absolute value of the deviation being less than 0.35 are mixed at the same (or equivalent) volume.

In another preferable embodiment, the number of said multiple parts sera in said step 1) is at least 300, more preferably at least 500.

In another aspect, the invention also provides a serum mixture prepared by the method according to the present invention. More particularly, when sIgE value of each serum mixture obtained by the method according to the invention is determined by Unicap method, the standard error is less than 3.90, more preferably less than 3.01. When sIgE value of each serum mixture is determined by ELISA method, the standard error is less than 0.040, more preferably less than 0.025.

In another aspect, the invention also relates to a kit for detecting the allergen potency. Said kit comprises the above standardized serum mixture obtained by the method according to the invention.

In still another aspect, the invention relates to the use of standardized serum mixture obtained by the method according to the invention in detecting the allergen potency. In one preferable embodiment, said allergen is the one in an allergen preparation used for detection. In another preferable embodiment, said allergen is the one in an allergen preparation used for treatment.

The invention has the advantages that the serum mixture which has relatively stable sIgE content may be obtained by using the methods according to the invention, so that said mixture may be used as a reliable standard in standardized production of allergen preparation, and the quality control of allergen preparation may be ensured.

MODES OF CARRYING OUT INVENTION

Figure 1:
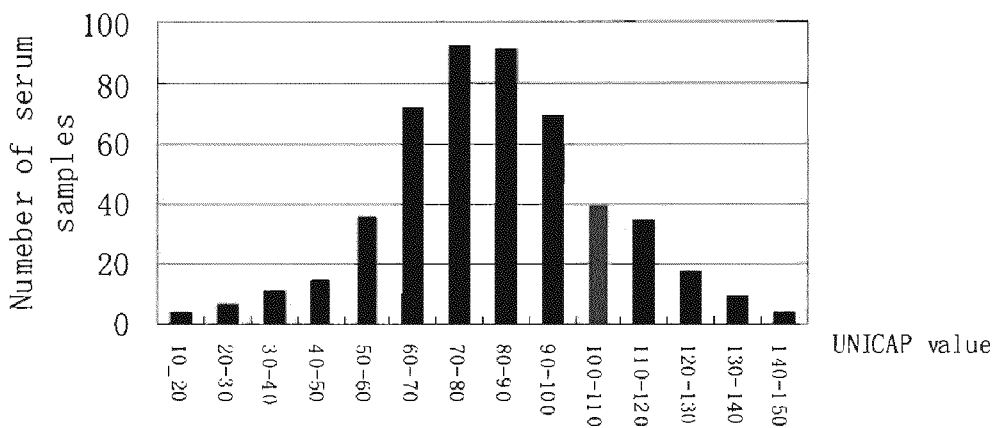
FIG. 1 shows the distribution of relative content of serum sIgE determined by Unicap method described in the invention.

The invention provides a method for preparing a standardized serum mixture for detecting allergen potency, which comprises the following steps:

1) providing multiple serum samples from multiple patients moderately hypersensitive to said allergen;

2) determining the relative content of said allergen-sIgE in each serum sample, and obtaining the mean value of the relative content of sIgE in said sera as well as the deviation value of the relative content of sIgE in each serum with respect to said mean value;

3) removing at least 5% of the serum samples with the largest and smallest deviation values respectively, and mixing the residual sera in the same volume.

Firstly, multiple serum samples are required. The inventor found that the number of serum samples should be 300 or more, preferably 500 or more, more preferably 1000 or more, based on lots of experiments and theory of statistics.

Said serum samples shall be obtained from multiple specific individual. Said individual may be a human or any other non-human mammal, including domestic animals, farm animals, non-human primates, zoo or sports ground animals, pets such as dog or feline, etc, with human being preferred. Said individual should demonstrate allergic reaction to said allergen, preferably moderate allergic reaction to said allergen, or have moderate allergic disease.

The term "allergen" as used herein refers to an allergen mixture containing many components from the same source. The source of allergen includes, but is not limited to, a variety of allergen from various pollens, dust mites, foods, insects, fungi, cockroaches, animal danders, etc. Said allergen is commercially available, or may be obtained by common extraction methods known in the art. For example, if the standardized serum mixture prepared is used to detect the allergen potency of *dermatophagoides farinae* allergen preparation, *dermatophagoides farinae* allergen prick-test reagent commercially available may be used in step 1). Likewise, the relative content of sIgE determined in step 2) is the relative content of specific IgE against the *dermatophagoides farinae* allergen.

The term "moderate hypersensitive" has the meaning generally recognized by a person skilled in the art. One way to determine whether a patient is a moderate hypersensitive patient is to apply an allergen skin prick-test to the individual and then determine whether the grade of reaction in said individual is +++. Skin prick-test is a common assay to determine the degree of allergic reaction of patient in vivo, which can not only identify the source of allergen to which the patient is hypersensitive, but also determine the degree (grade) with which the patient is hypersensitive to the allergen, and each grade is well known by the skilled person in the art. If the skin at the site receiving prick-test appears wheal or aula (flare), it is considered as positive reaction. The wheal means a bump surrounded by aula on the skin appeared upon contact with allergen. If the wheal is significant, then the area of wheal is compared; while if the wheal is not significant, then the area of aula is compared. Then, according to the ratio of area of wheal (aula) caused by allergen and positive control, the grade of reaction is determined as follows: if the ratio is 0-25% or it is the same as negative control, the grade is (−); if the ratio is 26-50%, the grade is (+); if the ratio is 51-100%, the grade is (++); if the ratio is 101-200%, the grade is (+++); if the ratio is more than 200%, the grade is (++++). In a preferable embodiment, grade +++ refers to the degree (the area of wheal or aula) with which the patient responds to the allergen is approximately the same as positive control (such as histamine phosphate).

Allergen prick-test reagent commercially available may be used by the skilled person in the art to perform the assay said above. In a preferable embodiment, physiological saline is used as negative control and 1-5 mg/ml histamine phosphate/histamine hydrochloride (preferably, 1.7 mg/ml histamine phosphate) is used as positive control. Allergen prick-test fluid is also used, the major ingredients of which are the same as the source of allergen to be tested. The concentration of protein in allergen prick-test fluid is related to the source of the allergen, generally between the range of 0.1-20 mg/ml, which may be determined by the skilled person in the art according to specific condition. For example, preferably, the concentration of protein for *Dermatophagoids farine* allergen prick-test fluid extracted from metabolism medium is about 1.0 mg/ml; the concentration of protein of *Dermatophagoids Pteronyssinus* allergen prick-test fluid extracted from the mite body is about 0.5 mg/ml. Of course, the grade of skin prick-test reaction may be determined by the skilled person in the art through other index or parameter.

When the reaction grade of patients is determined as +++ or the degree of reaction (area of wheal or aula) is approximately the same as positive control by allergen skin prick-test, the blood samples from these patients are collected by conventional means, separated by centrifugation, and then serum samples are obtained.

The relative content of sIgE in each serum sample obtained above is then determined. In the present invention, the term "relative content of sIgE", "sIgE content" or "sIgE value" can be used interchangeably. The determining methods well known in the art include, but are not limited to, enzyme-linked immunosorbent inhibitory assay (ELISA), radioallergosorbent test (RAST inhibitory test), and many novel in vitro assays developed based thereon, such as MAST, FAST as well as Pharma-CAP. In the embodiments of the invention, the relative content of sIgE in serum against said allergen is determined by Unicap method or ELISA method. Unicap method is performed according to the specification of Immun CAP Diagnostic System (UniCAP system) for automatically detecting allergen in vitro (Pharmacia, Sweden).

Subsequently, the mean value of relative content of sIgE for multiple serum samples (such as at least 300, preferably 500, more preferably 1000 samples) and the deviation values of relative content of sIgE for each serum with respect to said mean value are calculated. At least 5% (preferably 10%, more preferably 20%, even more preferably 30%) of serum samples with the largest and smallest deviation values were removed respectively, and the residual sera are mixed at the same volume (isometrically).

The term "deviation value" as used herein refers to the value by subtracting the mean value of multiple sera sIgE values from each serum sIgE value. It may be understood that the "deviation value" may be positive or negative.

In an embodiment of the invention, the relative content of serum sIgE is determined by Unicap method, and the mean value thereof is usually between 75-85. Then, the sera with the absolute value of the deviation less than 30 (i.e., the relative content of serum sIgE is between 45-115) may be mixed at the same volume; preferably, sera with the absolute value of the deviation less than 20 (i.e., the relative content of serum sIgE is between 55-105) may be mixed at the same volume; more preferably, sera with the absolute value of the deviation less than 15 (i.e., the relative content of serum sIgE is between 60-300) may be mixed at the same volume.

In another embodiment of the invention, the relative content of serum sIgE is determined by ELISA method, and the mean value thereof is usually between 0.9-1.0. Sera with the absolute value of the deviation less than 0.35 (i.e., the relative content of serum sIgE is between 0.55-3.35) may be mixed at the same volume; preferably, sera with the absolute value of the deviation less than 0.25 (i.e., the relative content of serum sIgE is between 0.65-1.25) may be mixed at the same volume; more preferably, sera with the absolute value of the deviation less than 0.15 (i.e., the relative content of serum sIgE is between 0.75-1.15) may be mixed at the same volume.

Figure 2:
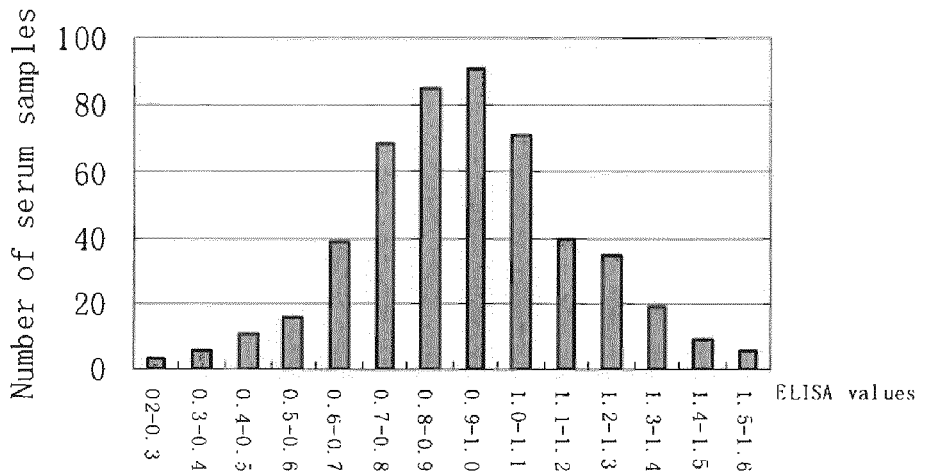
FIG. 2 shows the distribution of relative content of serum sIgE determined by ELISA method described in the invention.

FIGS. 1 and 2 show the distribution of relative content of serum sIgE determined by Unicap method and ELISA method described above, respectively (in the case of 500 serum samples), wherein horizontal axis represents the relative content of sIgE, and vertical axis represents the number of serum samples. The skilled person in the art may appreciate that the results in FIGS. 1 and 2 only demonstrate the results of specific experiments. These results are provided to facilitate the skilled person in the art understand the invention more clearly, but not meant to limit the invention to these specific values.

In another embodiment of the invention, the clinical symptoms of a patient may be employed to ascertain whether the patient is a moderate hypersensitive patient. In the case of allergic rhinitis, a moderate hypersensitive patient has the following clinical symptoms: perennial onset, having three major clinical manifestations, such as sneeze (more than 3 times in a raw), nose running and swelling of nasal mucosa, the number of days of onset in one year adding up to more than 6 months, the duration of onset in a day adding up to more than 0.5 hour, at least 1 year of course of disease, having definite inhalant sensitinogen, having individual and/or familial allergic disease history, and so on. Then, serum sIgE reaction of said patient is determined in vitro to ascertain sensitinogen (allergen). The determining methods well known in the art include, but are not limited to, enzyme linked immunosorbent inhibitory assay (ELISA), radioallergosorbent inhibitory test (RAST inhibitory test), and many novel in vitro assays developed based on it, such as MAST, FAST as well as Pharma-CAP.

In an embodiment of the invention, the relative content of serum sIgE for patients is determined by Unicap method or ELISA method. Multiple (such as at least 300, preferably 500, more preferably 1000) serum samples in accord with the following criteria are selected: the serum sIgE value within 1-200 (preferably 10-150) through Unicap assay, or the serum sIgE value within 0.10-2.50 (preferably 0.20-1.60) through ELISA assay. The mean of relative content of sIgE for multiple serum samples and the deviation value for each serum relative to said mean are calculated. At least 5% (preferably 10%, more preferably 20%, even more preferably 30%) serum samples with the largest and smallest deviation value were removed respectively, and the residual sera are mixed at the same volume.

Therefore, in another aspect, the invention relates to a method for preparing serum mixture used to detect allergen potency, said method comprising the following steps:

1) serum samples from patients diagnosed as having clinical symptoms of allergic disease or allergic reaction to said allergen are provided; the relative content of serum sIgE for patients said above is determined by Unicap method or ELISA method; multiple (such as at least 300, preferably 500, more preferably 1000) serum samples having the relative content of sIgE within 1-200 (preferably 10-150) determined by Unicap assay, or having the relative content of sIgE within 0.10-2.50 (preferably 0.20-1.60) determined by ELISA assay are selected;

2) the mean of relative content of sIgE for said multiple sera selected and the deviation value of relative content of sIgE for each serum relative to said mean are calculated;

3) at least 5% serum samples with the largest and smallest deviation value were removed respectively, and the residual sera are mixed at the same volume.

The serum mixture obtained by the invention may be used as standardized serum pool for detecting allergen potency. As validated in examples, the sIgE content in the serum mixture produced by the method of the invention is stable, that is, if sIgE value of each serum mixture is determined by Unicap method, the sample standard deviation is less than 3.90, more preferably less than 3.01; if sIgE value of each serum mixture is determined by ELISA method, the sample standard deviation is less than 0.040, more preferably less than 0.025.

The term "sample standard deviation" is used statistically to measure fluctuation of one sample. The less the sample standard deviation, the less the sample data fluctuate, i.e. the more stable the sample data is. The computation formula for it is:

$$S = \sqrt{\frac{\sum_{i=1}^{n}(x_i - \bar{x})^2}{n-1}}$$

wherein, S represents sample standard deviation, $\bar{x}$ represents the arithmetic mean of sample, n represents the number of samples, $x_i$ represents the value of each sample.

Of course, the skilled person in the art may employ other conventional statistic index, for example but are not limited to, sample variance, population variance, population standard deviation etc, to ascertain the stability of sIgE content in serum mixture produced by the method of the invention.

The invention further relates to serum mixture obtained using the methods according to the invention, and the use of said serum mixture in detecting allergen potency, for example to determine the potency of allergen preparation for detection, to determine the potency of allergen preparation for treatment, in particularly, to detect the allergen potency during the production of allergen preparation as standard for controlling the quality of allergen.

The source of allergen includes, but is not limited to, allergen from pollens, dust mites, foods, insects, fungi, cockroaches, animal danders, etc. These allergens may be commercially available, or may be obtained by common extraction methods known in the art.

In an embodiment of the invention, the source of said allergen preparation is *Dermatophagoids farine*. Said allergen may be prepared by the following method: grow *Dermatophagoids farine* in culture medium for dust mite to a certain density; wash the body of dust mites with physiological saline; triturate the body in liquid nitrogen after airing; degrease with acetone until the acetone becomes colorless; extract the mite body with physiological saline for 60-80 hours; filtrate, and the filtrate generated is *Dermatophagoids farine* allergen extract. Then *Dermatophagoids farine* allergen preparation is obtained by mixing said extract with pharmaceutically acceptable carrier.

In another embodiment of the invention, the source of said allergen preparation is *Artemisia* pollen. Said allergen may be prepared by the following method: degrease *Artemisia* pollen with acetone until acetone becomes colorless upon standing, remove the acetone, dry the pollen, extract with carbonate-saline for 40-60 hours, filtrate, and the supernatant liquid collected is *Artemisia* pollen allergen extract. Then *Artemisia* pollen allergen preparation is obtained by mixing said extract with pharmaceutically acceptable carrier.

The principle of using the standardized serum mixture produced by the method of the invention to detect allergen potency is as follows: hypersensitive patients may produce in vivo specific IgE (sIgE) against allergen. The allergen active ingredients in the preparation to be tested will bind to sIgE in the serum of a patient having hypersensitivity disease to form a complex, resulting in the concentration of free sIgE in serum decrease. Then, sIgE content in serum against the allergen is detected. The greater the allergen potency in the preparation to be tested, the more the sIgE concentration reduces after the serum of patient reacts with the preparation. Free sIgE in the serum of patient will reduce correspondingly when detected by UniCAP system or ELISA method. The allergen potency in the preparation to be tested may be obtained by comparing sIgE concentration in the serum of patient before and after the preparation is added. Under the condition that sIgE in the serum is not thoroughly bound by allergen in the preparation to be tested, there is a positive correlation between the concentration of allergen and the decrease of sIgE concentration in the serum of a patient during this process. The potency of allergen in the preparation to be tested may be determined according to the inhibitory ratio of sIgE. The higher the inhibitory ratio of sIgE, the higher the allergen potency in the preparation to be tested is.

In a further aspect, the invention relates to a kit used to detect allergen potency, said kit comprising the standardized serum mixture prepared by the method of the invention. In one embodiment, said kit for detecting allergen potency is a detection kit based on ELISA method, which determines the potency of allergen by calculating the inhibitory ratio of sIgE. Said kit comprises: the standardized serum mixture produced by the method of the invention, ELISA microplates (pre-coated with said allergen), washing solution, blocking solution, developing solution, terminating buffer, goat anti-human IgG, goat anti-human IgE-HRP, etc. In the above kit, the standardized serum mixture is produced by the method of the invention, while the other reagents or consumables may be commercially available.

It may be appreciated that the principle of kits for detecting said allergen potency described in the invention is well known in the art. In addition to ELISA method, it may further include, but not limited to, radioallergosorbent inhibitory test (RAST inhibitory test), and many novel assays for detecting sIgE in vitro which are developed based thereon, such as MAST, FAST as well as Pharma-CAP.

In the following, the invention will be described in further detail with reference to the examples. It is to be understood that these examples are provided for illustration and not for limiting the scope of the invention.

EXAMPLE 1

Collection of Serum Hypersensitive to *Dermatophagoids farine*

Allergen prick-test reagent is provided by Biology Laboratory of Shanghai Medical University. The reagent includes physiological saline (negative control), histamine phosphate (positive control), and *Dermatophagoids farine* prick-test fluid.

Step: (1) The skin from left forearm on the side of the palm is selected for performing the prick-test. (2) The name of the prick-test fluid is marked at the middle part of left forearm with a marker pen, and the distance between two prick-test fluids is not less than 5 cm in order to prevent overlapping of aula; and then the skin is disinfected. (3) A drop of prick-test fluids (larger than the tip of a lancet) is dropped from bottom to top. (4) The skin is gently pricked (without bleeding) by a sterile disposable prick lancet through the drop perpendicularly, discard the lancet after 1 second, wipe off all the drops after 5 minutes, and then observe and record the skin reaction after 30 minutes.

Criteria for determining positive results: the grade of reaction is determined by the ratio of the area of wheals caused by *Dermatophagoids farine* prick-test fluid and histamine phosphate (positive control fluid). No reaction or reaction the same size as the negative control, is indicated by (−); (+) is larger than ¼ the size of the histamine phosphate (positive control); and (++) is larger than ½ the size; A wheal reaction approximately the same size as the positive control is graded (+++); and (++++) is larger than 2 times the size.

2 ml of blood samples from the patients whose reaction grade are (+++) are collected, centrifuged at 5000 rpm, 4° C. for 10 minutes, and the serum in superstratum is pipetted out gently.

EXAMPLE 2

Determination of Relative Content of sIgE Against *Dermatophagoids farine* Allergen in Serum from Patients (1) Unicap method is used (according to the specification of Immun CAP Diagnostic System Uni CAP system for automatically detecting allergen in vitro, Pharmacia, Sweden) to detect the relative content of sIgE against *Dermatophagoids farine* allergen sIgE in the serum from patients.

(2) ELISA method is used to detect the relative content of sIgE against *Dermatophagoids farine* allergen in the serum from patients.

*Dermatophagoids farine* in medium of dust mite is grow to the density of 300-500/g (medium). The dust mite body obtained is then suspended and washed in physiological saline, then air-dried, weighed, triturated in liquid nitrogen, and then soaked in acetone to degrease for three times continuously, each 4 hours, until the acetone becomes colorless. The solid after degreasing is air-dried until there is no odor of acetone and it is weighed. The body of *Dermatophagoids farine* is extracted by physiological saline in 1:25 (W/V) (25 ml physiological saline is used for 1 g degreased body of *Dermatophagoids farine*), magnetically agitating for 72 hours at 4° C. intermittently (agitating for 8 hours each time, standing overnight and magnetically agitating for another 8 hours, repeatedly). After filtration sterilization, the filtrate is used as *Dermatophagoids farine* allergen extract. The content of protein in the extract is determined by BCA protein assay kit (Pierce). The *Dermatophagoids farine* allergen extract is diluted with coating buffer, and the concentration of protein is adjusted to 0.3-2 mg/ml, preferably, about 0.8 mg/ml.

100 ul *Dermatophagoids farine* allergen extract diluted with coating buffer is added into each well of ELISA plate, and then it is incubated for 1.5-2 hours at 37° C., and standing at 4° C. overnight. The ELISA plate is removed and standing at room temperature for 20 minutes for equilibrating with the room temperature. The plate is washed with wash buffer on plate-washer for 5 times, and the excess wash buffer is tapped out without drying the plate (by banging the ELISA plate upside down on dry paper towel before new reagent is added during the assay). Blocking solution is added (200 ul/well) and then it is incubated for 2 hours at room temperature. The serum is prepared as follows after blocking reaction being performed for one hour: the serum collected from patients is diluted with blocking solution at a ration of 1:20; goat anti-human IgG (polyclonal antibody) is diluted to 5 ug/ul with blocking solution; to each 100 ul diluted serum, 50 ug goat anti-human IgG is added; and mix gently. The plate is incubated for 45 minutes at room temperature. The blocking solution in the wells of the plate is washed off with wash buffer on plate-washer (5 times), dried by tapping, 100 ul serum prepared above (mixed by shaking up and down for 2-3 times prior to loading) is added, and then the plate is incubated for 2 hours at room temperature. The plate is washed with wash buffer for 5 times, dried by tapping, and 100 ul 1:1000 goat anti-human IgE-HRP is added, and the plate is incubated for 1 hours at room temperature. The blocking solution in the wells of the plate is washed off with wash buffer on plate-washer (5 times). 100 ul of TMB developing solution that is extemporaneously prepared is added sequentially into each well. The plate is mixed gently and developed for 15 minutes in darkness. 100 ul/well of 2 M $H_2SO_4$ is added to quench the reaction and the reading data at 450 nm is obtained.

EXAMPLE 3

Blending *Dermatophagoids farine* Positive Serum (1) 300 serum samples from patients whose reaction grade of skin test is +++ are collected according to the method in example 1. The relative content of sIgE against *Dermatophagoids farine* allergen is determined by Unicap method in example 2. The mean value of sIgE for 300 serum samples and the deviation value of the relative content of sIgE of each serum with respect to said mean value is calculated. The serum samples with the absolute value of the deviation less than 30 are mixed at the same volume. Three serum mixtures are prepared by the same method and used in example 4.

(2) 300 serum samples from patients whose reaction grade of skin test is +++ are collected according to the method in example 1. The relative content of sIgE against *Dermatophagoids farine* allergen is determined by ELISA method in example 2. The mean value of sIgE for 300 serum samples and deviation value of the relative content of sIgE of each serum with respect to said mean value is calculated. The serum samples with the absolute value of the deviation less than 0.35 are mixed at the same volume. Three serum mixtures are prepared by the same method and used in example 4.

(3) 30, 100 and 500 serum samples from patients whose reaction grade of skin test is +++ are collected respectively according to the method in example 3. Procedures of step (1) and (2) are repeated. Three serum mixtures are used in example 4.

EXAMPLE 4

Determination of the Relative Content of sIgE Against *Dermatophagoids farine* Allergen in *Dermatophagoids farine* Positive Serum Mixture 1. Serum mixtures prepared from 30 serum samples are obtained (from example 3).

(1) The content of sIgE in serum mixture is determined by Unicap method.

| Serum mixture | Serum mixture 1 prepared by Unicap method | Serum mixture 2 prepared by Unicap method | Serum mixture 3 prepared by Unicap method | Serum mixture 1 prepared by ELISA method | Serum mixture 2 prepared by ELISA method | Serum mixture 3 prepared by ELISA method | Sample standard deviation |
|---|---|---|---|---|---|---|---|
| The relative content of sIgE is determined by Unicap (KUA/L) | 93.79 | 69.58 | 85.31 | 76.78 | 73.49 | 90.87 | 9.816 |

(2) The content of sIgE in serum mixture is determined by ELISA method.

| Serum mixture | Serum mixture 1 prepared by Unicap method | Serum mixture 2 prepared by Unicap method | Serum mixture 3 prepared by Unicap method | Serum mixture 1 prepared by ELISA method | Serum mixture 2 prepared by ELISA method | Serum mixture 3 prepared by ELISA method | Sample standard deviation |
|---|---|---|---|---|---|---|---|
| The relative content of sIgE is determined by ELISA | 0.97 | 0.80 | 0.87 | 0.83 | 0.81 | 0.95 | 0.073 |

2. Serum mixtures prepared from 100 serum samples are obtained (from example 3).

(1) The content of sIgE in serum mixture is determined by Unicap method.

| Serum mixture | Serum mixture 1 prepared by Unicap method | Serum mixture 2 prepared by Unicap method | Serum mixture 3 prepared by Unicap method | Serum mixture 1 prepared by ELISA method | Serum mixture 2 prepared by ELISA method | Serum mixture 3 prepared by ELISA method | Sample standard deviation |
|---|---|---|---|---|---|---|---|
| The relative content of sIgE is determined by Unicap (KUA/L) | 77.18 | 87.63 | 78.73 | 87.96 | 84.49 | 85.06 | 4.540 |

(2) The content of sIgE in serum mixture is determined by ELISA method.

| Serum mixture | Serum mixture 1 prepared by Unicap method | Serum mixture 2 prepared by Unicap method | Serum mixture 3 prepared by Unicap method | Serum mixture 1 prepared by ELISA method | Serum mixture 2 prepared by ELISA method | Serum mixture 3 prepared by ELISA method | Sample standard deviation |
|---|---|---|---|---|---|---|---|
| The relative content of sIgE is determined by ELISA | 0.86 | 0.95 | 0.85 | 0.93 | 0.86 | 0.94 | 0.046 |

3. Serum mixtures prepared from 300 serum samples are obtained (from example 3).

(1) The content of sIgE in serum mixture is determined by Unicap method,

| Serum mixture | Serum mixture 1 prepared by Unicap method | Serum mixture 2 prepared by Unicap method | Serum mixture 3 prepared by Unicap method | Serum mixture 1 prepared by ELISA method | Serum mixture 2 prepared by ELISA method | Serum mixture 3 prepared by ELISA method | Sample standard deviation |
|---|---|---|---|---|---|---|---|
| The relative content of sIgE is determined by Unicap (KUA/L) | 78.36 | 86.98 | 87.56 | 82.39 | 79.26 | 84.69 | 3.876 |

(2) The content of sIgE in serum mixture is determined by ELISA method.

| Serum mixture | Serum mixture 1 prepared by Unicap method | Serum mixture 2 prepared by Unicap method | Serum mixture 3 prepared by Unicap method | Serum mixture 1 prepared by ELISA method | Serum mixture 2 prepared by ELISA method | Serum mixture 3 prepared by ELISA method | Sample standard deviation |
|---|---|---|---|---|---|---|---|
| The relative content of sIgE is determined by ELISA | 0.85 | 0.92 | 0.94 | 0.87 | 0.85 | 0.91 | 0.038 |

4. Serum mixtures prepared from 500 serum samples are obtained (from example 3).

(1) The content of sIgE in serum mixture is determined by Unicap method.

| Serum mixture | Serum mixture 1 prepared by Unicap method | Serum mixture 2 prepared by Unicap method | Serum mixture 3 prepared by Unicap method | Serum mixture 1 prepared by ELISA method | Serum mixture 2 prepared by ELISA method | Serum mixture 3 prepared by ELISA method | Sample standard deviation |
|---|---|---|---|---|---|---|---|
| The relative content of sIgE is determined by Unicap (KUA/L) | 79.35 | 85.21 | 82.16 | 86.73 | 79.68 | 84.22 | 3.009 |

(2) The content of sIgE in serum mixture is determined by ELISA method.

| | Serum mixture | | | | | | |
|---|---|---|---|---|---|---|---|
| | Serum mixture 1 prepared by Unicap method | Serum mixture 2 prepared by Unicap method | Serum mixture 3 prepared by Unicap method | Serum mixture 1 prepared by ELISA method | Serum mixture 2 prepared by ELISA method | Serum mixture 3 prepared by ELISA method | Sample standard deviation |
| The relative content of sIgE is determined by ELISA | 0.86 | 0.91 | 0.86 | 0.88 | 0.90 | 0.87 | 0.021 |

Conclusion may be drawn from the above results that if 300 serum samples of patients are obtained, the content of sIgE specific to *Dermatophagoids farine* in six *Dermatophagoids farine* positive serum mixtures prepared according to the two methods in example 3 is stable. That is, when sIgE value in each serum mixture is determined by Unicap method, sample standard deviation is less than 3.90. When sIgE value in each serum mixture is determined by ELISA method, sample standard deviation is less than 0.040. The relative content of sIgE of the serum mixtures prepared from 500 serum samples is more stable.

EXAMPLE 5

Collection of Serum Hypersensitive to *Artemisia* pollen

Allergen prick-test reagent is provided by Biology Laboratory of Shanghai Medical University. The reagent includes physiological saline (negative control), histamine phosphate (positive control), and *Artemisia* pollen prick-test fluid.

Step: (1) The skin from left forearm on the side of the palm is selected for performing the prick-test. (2) The name of the prick-test fluid is marked at the middle part of left forearm with a marker pen, and the distance between two prick-test fluids is not less than 5 cm in order to prevent overlapping of aula; and then the skin is sterilized. (3) A drop of prick-test fluids (larger than the tip of a lancet) is dropped from bottom to top. (4) The skin is gently pierced (without bleeding) by a sterilized one-time prick-test lancet through the drop perpendicularly, discard the lancet after 1 second, wipe off all the drops after 5 minutes, and observe and record the skin reaction after 30 minutes.

Criteria for determining positive results: the grade of reaction is determined by the ratio of the area of wheals caused by *Artemisia* pollen prick-test fluid and histamine phosphate (positive control fluid). No reaction or reaction the same size as the negative control, is indicated by (−); (+) is larger than ¼ the size of the histamine phosphate (positive control); and (++) is larger than ½ the size; A wheal reaction approximately the same size as the positive control is graded (+++); and (++++) is larger than 2 times the size.

2 ml blood from the patients whose reaction grade is (+++) is collected, centrifuged at 5000 rpm 4° C. for 10 minutes, and the serum in superstratum is pipetted out gently.

EXAMPLE 6

Determination of Relative Content of sIgE Against *Artemisia* Pollen Allergen sIgE in Serum from Patients (1) Unicap method is used (according to the specification of Immun CAP Diagnostic System Uni CAP system for automatically detecting allergen in vitro, Pharmacia, Sweden) to detect the relative content of sIgE against *Artemisia* pollen allergen in the serum from patients.

(2) ELISA method is used to detect the relative content of sIgE against *Artemisia* pollen allergen in the serum from patients.

*Artemisia* pollen is collected and air dried to constant weight. A certain amount of pollen is weighed accurately into conical flask. After adding 3-4 (W/V) volumes of acetone into the flask, the flask is shaken at 180 rpm for 1.5 hours, then stands for 30 minutes. The acetone in upper layer is decanted gently, fresh acetone is added and the conical flask is shaken again, until the acetone in upper layer becomes colorless upon standing. The acetone is decanted as much as possible. The pollen is transferred to a large culture dish and dried in fuming cupboard for 4 hours, until powder forms and there is no odor of acetone. The powder is collected, weighed and stored at 4° C. A certain amount of degreased pollen is weighed accurately into conical flask. Carbonate-saline for extraction is added in the ratio of 1:30 (W/V) and stirred on a magnetic stirring apparatus for 48 hours. The suspension is taken out and centrifuged at 10,000 rpm for 20 minutes at 4° C. The supernatant is collected, and *Artemisia* pollen extract is obtained upon filtration sterilization of supernatant through 0.45 um filter. The content of protein in the extract is determined by BCA method. The *Artemisia* pollen extract is diluted with coating buffer, and the content of protein is adjusted to 0.05-0.3 mg/ml, preferably, 0.1 mg/ml.

100 ul *Artemisia* pollen extract diluted with coating buffer is added into each well of ELISA plate which is then incubated for 1.5-2 hours at 37° C. and stands overnight at 4° C. The ELISA plate is removed and stands at room temperature for 20 minutes for equilibrating with the room temperature. The plate is washed with wash buffer on plate-washer for 5 times, and the water is tapped without drying the plate (the ELISA plate is placed on a clean absorbent paper facing downwards before new reagent is added during the assay). Blocking solution is added (200 ul/well), and the plate is incubated at room temperature for 2 hour. After blocking reaction being performed for one hour, the serum is prepared as follows: the sera collected from patients is diluted with blocking solution at the ratio of 1:20; goat anti-human IgG (polyclonal antibody) is diluted to 5 ug/ul with blocking solution: 50 ug goat anti-human IgG is added to each 100 ul of diluted serum; and then the mixture is mixed gently. The plate is incubated at room temperature for 45 minutes. The blocking solution in the wells of the plate is washed off with wash buffer on plate-washer (5 times), dried by tapping, and then 100 ul of serum prepared above (mixed by shaken up and down for 2-3 times prior to loading) is added. The plate is incubated for 2 hours at room temperature, washed with wash buffer for 5 times, and dried by tapping. 100 ul of 1:1000 goat anti-human IgE-HRP is added, and then the plate is incubated for 1 hours at room temperature. The blocking solution in the wells of the plate is washed off with wash buffer on plate-washer (5 times). 100 ul of 1 MB developing solution which is extemporaneously prepared is added sequentially into each well, mix gently and develop for 15 minutes in darkness. 100 ul/well of 2 M $H_2SO_4$ is added to quench the reaction and the reading data at 450 nm is obtained.

EXAMPLE 7

Blending *Artemisia* Pollen Positive Serum (1) 300 serum samples from patients whose reaction grade of skin test is +++ are collected according to the method in Example 5. The relative content of sIgE against *Artemisia* pollen allergen is determined by Unicap method in Example 6. The mean value of sIgE for 300 serum samples and deviation value of the relative content of sIgE in each serum with respect to said mean value are calculated. At least 5% serum samples with the largest and smallest deviation values are removed respectively, and then the residual serum samples are mixed at the same volume. Three serum mixtures are prepared by the same method and used in Example 8.

(2) 300 serum samples from patients whose reaction grade of skin test is +++ are collected according to the method in example 5. The relative content of sIgE against *Artemisia* pollen allergen is determined by ELISA method in Example 6. The mean value of sIgE for 300 serum samples and deviation value of the relative content of sIgE in each serum with respect to said mean value are calculated. At least 5% serum samples with the largest and smallest deviation values are removed respectively, and the residual sera are mixed at the same volume. Three serum mixtures are prepared by the same method and used in example 8.

(3) 30, 100 and 500 serum samples from patients whose reaction grade of skin test is +++ are collected respectively, according to the method in Example 5. Procedures of step (1) and (2) are repeated. Three serum mixtures are used in Example 8.

EXAMPLE 8

Determination of the Relative Content of sIgE Against *Artemisia* Pollen Allergen in *Artemisia* Pollen Positive Serum Mixture 1. Serum mixtures prepared from 30 serum samples are obtained (from Example 7).

(1) The content of sIgE in serum mixture is determined by Unicap method.

|  | Serum mixture | | | | | | |
|---|---|---|---|---|---|---|---|
|  | Serum mixture 1 prepared by Unicap method | Serum mixture 2 prepared by Unicap method | Serum mixture 3 prepared by Unicap method | Serum mixture 1 prepared by ELISA method | Serum mixture 2 prepared by ELISA method | Serum mixture 3 prepared by ELISA method | Sample standard deviation |
| The relative content of sIgE is determined by Unicap (KUA/L) | 75.79 | 93.84 | 71.63 | 88.93 | 76.74 | 87.17 | 8.809 |

(2) The content of sIgE in serum mixture is determined by ELISA method.

|  | Serum mixture | | | | | | |
|---|---|---|---|---|---|---|---|
|  | Serum mixture 1 prepared by Unicap method | Serum mixture 2 prepared by Unicap method | Serum mixture 3 prepared by Unicap method | Serum mixture 1 prepared by ELISA method | Serum mixture 2 prepared by ELISA method | Serum mixture 3 prepared by ELISA method | Sample standard deviation |
| The relative content of sIgE is determined by ELISA | 0.83 | 0.97 | 0.81 | 0.94 | 0.87 | 0.94 | 0.066 |

2. Serum mixtures prepared from 100 serum samples are obtained (from Example 7).

(1) The content of sIgE in serum mixture is determined by Unicap method.

|  | Serum mixture | | | | | | |
|---|---|---|---|---|---|---|---|
|  | Serum mixture 1 prepared by Unicap method | Serum mixture 2 prepared by Unicap method | Serum mixture 3 prepared by Unicap method | Serum mixture 1 prepared by ELISA method | Serum mixture 2 prepared by ELISA method | Serum mixture 3 prepared by ELISA method | Sample standard deviation |
| The relative content of sIgE is determined by Unicap (KUA/L) | 78.65 | 86.75 | 84.19 | 88.23 | 77.17 | 87.86 | 4.805 |

(2) The content of sIgE in serum mixture is determined by ELISA method.

|  | Serum mixture | | | | | | |
|---|---|---|---|---|---|---|---|
|  | Serum mixture 1 prepared by Unicap method | Serum mixture 2 prepared by Unicap method | Serum mixture 3 prepared by Unicap method | Serum mixture 1 prepared by ELISA method | Serum mixture 2 prepared by ELISA method | Serum mixture 3 prepared by ELISA method | Sample standard deviation |
| The relative content of sIgE is determined by ELISA | 0.87 | 0.93 | 0.86 | 0.94 | 0.85 | 0.95 | 0.045 |

3. Serum mixtures prepared from 300 serum samples are obtained (from Example 7).

(1) The content of sIgE in serum mixture is determined by Unicap method.

|  | Serum mixture | | | | | | |
|---|---|---|---|---|---|---|---|
|  | Serum mixture 1 prepared by Unicap method | Serum mixture 2 prepared by Unicap method | Serum mixture 3 prepared by Unicap method | Serum mixture 1 prepared by ELISA method | Serum mixture 2 prepared by ELISA method | Serum mixture 3 prepared by ELISA method | Sample standard deviation |
| The relative content of sIgE is determined by Unicap (KUA/L) | 87.08 | 79.15 | 83.78 | 78.56 | 87.57 | 84.50 | 3.841 |

(2) The content of sIgE in serum mixture is determined by ELISA method.

|  | Serum mixture | | | | | | |
|---|---|---|---|---|---|---|---|
|  | Serum mixture 1 prepared by Unicap method | Serum mixture 2 prepared by Unicap method | Serum mixture 3 prepared by Unicap method | Serum mixture 1 prepared by ELISA method | Serum mixture 2 prepared by ELISA method | Serum mixture 3 prepared by ELISA method | Sample standard deviation |
| The relative content of sIgE is determined by ELISA | 0.93 | 0.86 | 0.87 | 0.85 | 0.94 | 0.91 | 0.038 |

4. Serum mixtures prepared from 500 serum samples are obtained (from Example 7).

(1) The content of sIgE in serum mixture is determined by Unicap method.

|  | Serum mixture | | | | | | |
|---|---|---|---|---|---|---|---|
|  | Serum mixture 1 prepared by Unicap method | Serum mixture 2 prepared by Unicap method | Serum mixture 3 prepared by Unicap method | Serum mixture 1 prepared by ELISA method | Serum mixture 2 prepared by ELISA method | Serum mixture 3 prepared by ELISA method | Sample standard deviation |
| The relative content of sIgE is determined by Unicap (KUA/L) | 78.65 | 83.14 | 82.42 | 80.59 | 79.48 | 82.50 | 1.830 |

(2) The content of sIgE in serum mixture is determined by ELISA method.

|  | Serum mixture | | | | | | |
|---|---|---|---|---|---|---|---|
|  | Serum mixture 1 prepared by Unicap method | Serum mixture 2 prepared by Unicap method | Serum mixture 3 prepared by Unicap method | Serum mixture 1 prepared by ELISA method | Serum mixture 2 prepared by ELISA method | Serum mixture 3 prepared by ELISA method | Sample standard deviation |
| The relative content of sIgE is determined by ELISA | 0.84 | 0.81 | 0.79 | 0.86 | 0.83 | 0.82 | 0.024 |

Conclusion may be drawn from the above results that, if 300 serum samples are obtained, the content of sIgE specific to *Artemisia* pollen in six *Artemisia* pollen positive serum mixtures prepared according to the two methods in Example 7 is stable. That is, if sIgE value in each serum mixture is determined by Unicap method, sample standard deviation is less than 3.90. When sIgE value in each serum mixture is determined by ELISA method, sample standard deviation is less than 0.040. The relative content of sIgE of the serum mixtures prepared from 500 serum samples is more stable.

EXAMPLE 9

Use of *Dermatophagoids farine* Hypersensitive Standardized Serum Mixture in Determining the Potency of *Dermatophagoids farine* Skin Prick-Test Fluid 100 ul *Dermatophagoids farine* Skin prick-test fluids from 3 batches (Tradename "Spotter", Zhejiang Wolwo Bio-Pharmaceutical Co., Ltd.) are mixed isometrically with *Dermatophagoids farine* hypersensitive standardized serum mixture (prepared by the method in Example 3 which is prepared from "500 serum samples") at the same volume, with the standardized serum mixture used as control. All the mixtures are incubated in an incubator at 37° C. for one hour, then left in a refrigerator at 4° C. overnight (9-12 hours). Then, the samples are transferred into a sterilized glass tube and the sIgE content is determined by Unicap100 Instrument. The relative content of sIgE for *Dermatophagoids farine* positive standardized serum is determined as 84.15. The results of determination upon mixing *Dermatophagoids farine* skin prick-test fluids with standardized serum mixture at the same volume are provided as follows:

| Lot number of Dermatophagoids farine prick-test fluid | Unicap value (KUA/L) | | | | Inhibitory ratio of sIgE |
|---|---|---|---|---|---|
|  | 1 | 2 | 3 | mean |  |
| 20060101 | 6.26 | 3.79 | 5.34 | 5.13 | 93.9% |
| 20060102 | 3.37 | 6.92 | 5.28 | 5.19 | 93.8% |
| 2006010 | 5.62 | 7.06 | 4.17 | 5.62 | 93.3% |

The potency of allergen in *Dermatophagoids farine* prick-test fluid may be obtained according to the inhibitory ratio of sIgE. The higher the inhibitory ratio of sIgE, the higher the potency of allergen is.

EXAMPLE 10

Use of *Dermatophagoids farine* Standardized Serum Mixture in Determining Poteney of *Dermatophagoids farine* Drop 100 μl Number 5 *Dermatophagoids farine* drops from 3 batches (Tradename "Chanllergen", Zhejiang Wolwo Bio-Pharmaceutical Co., Ltd.) are mixed isometrically with *Dermatophagoids farine* hypersensitive standardized serum mixture (prepared by the method in Example 3 which is prepared from "300 serum samples") respectively at the same volume, with the standardized serum mixture used as control. All the mixtures are incubated in an incubator at 37° C. for one hour, then left in a refrigerator at 4° C. overnight (9-12 hours). The samples left at 4° C. overnight are transferred into a sterilized glass tube and the sIgE content is determined by Unicap100 Instrument. The relative content of sIgE for *Dermatophagoids farine* positive standardized serum is determined as 83.72. The results of determination upon mixing *Dermatophagoids farine* drop with standardized serum mixture at the same volume are provided as follows:

| Lot number of Dermatophagoids farine drop | Unicap value (KUA/L) | | | | Inhibitory ratio of sIgE |
|---|---|---|---|---|---|
| | 1 | 2 | 3 | mean | |
| 20060401 | 15.21 | 13.95 | 18.42 | 15.86 | 81.0% |
| 20060402 | 14.76 | 16.72 | 10.20 | 13.89 | 83.4% |
| 20060403 | 15.66 | 18.34 | 14.33 | 16.11 | 80.8% |

The potency of allergen in *Dermatophagoids farine* drop may be obtained according to the inhibitory ratio of sIgE. The higher the inhibitory ratio of sIgE, the higher the potency of allergen is.

EXAMPLE 11

Use of *Artemisia* Pollen Standardized Serum Mixture in Determining Potency of *Artemisia* Pollen Skin Prick-Test Fluid

*Artemisia* pollen is collected and air dried to constant weight. A certain amount of pollen is weighed accurately into conical flask. After adding 3-4 (W/V) volumes of acetone into the flask, the flask is shaken at 180 rpm for 1.5 hours, then stands for 30 minutes. The acetone in upper layer is decanted gently, fresh acetone is added and the conical flask is shaken again, until the acetone in upper layer becomes colorless upon standing. The acetone is decanted as much as possible. The pollen is transferred to a large culture dish and dried in fuming cupboard for 4 hours, until powder forms and there is no odor of acetone. The powder is collected, weighed and reserved at 4° C. A certain amount of degreased pollen is weighed accurately into a conical flask. Carbonate-saline for extraction is added in the ratio of 1:30 (W/V) and stirred on a magnetic stirring apparatus for 48 hours. The suspension is taken out and centrifuged at 10,000 rpm for 20 minutes at 4° C. The supernatant is collected, and *Artemisia* pollen extract is obtained upon filtration sterilization of supernatant through 0.45 um filter. The content of protein in the extract is determined by BCA method. The *Artemisia* pollen extract is diluted with coating buffer, and the content of protein is adjusted to 0.05-0.3 mg/ml, preferably, 0.1 mg/ml.

100 ul *Artemisia* pollen extract diluted with coating buffer is added into each well of ELISA plate which is then incubated for 1.5-2 hours at 37° C. and stands overnight at 4° C. The ELISA plate is removed and stands at room temperature for 20 minutes for equilibrating with the room temperature. The plate is washed with wash buffer on plate-washer for 5 times, and the water is tapped without drying the plate (the ELISA plate is placed on a clean absorbent paper facing downwards before new reagent is added during the assay). Blocking solution is added (200 ul/well), and the plate is incubated at room temperature for 2 hour. After blocking reaction being performed for one hour, the serum is prepared as follows: the collected *Artemisia* pollen positive standardized serum (prepared by the method in Example 7 which is obtained from 300 serum samples) is diluted with blocking solution in the ratio of 1:20; goat anti-human IgG (polyclonal antibody) is diluted to 5 ug/ul with blocking solution; 50 ug goat anti-human IgG is added to each 100 ul of diluted serum; and then the mixture is mixed gently. The mixture is incubate at room temperature for 45 minutes. 100 ul of *Artemisia* pollen skin prick-test fluid (Zhejiang Wolwo Bio-Pharmaceutical Co., Ltd.) is mixed with the above serum samples at the same volume. The serum diluted and with IgG added is used as positive control. The mixtures and positive control are incubated in an incubator for one hour at 37° C. The blocking solution in the wells of the plate is washed off with wash buffer on plate-washer (5 times), dried by tapping, and then 100 ul of serum prepared above (mixed by shaken up and down for 2-3 times prior to loading) is added. The mixture is incubated for 2 hours at room temperature. The plate is washed with wash buffer for 5 times and dried by tapping. 100 ul of 1:1000 goat anti-human IgE-HRP is added, and the mixture incubated for 1 hours at room temperature. The blocking solution in the wells of the plate is washed off with wash buffer on plate-washer (5 times). 100 ul of TMB developing solution which is extemporaneously prepared is added sequentially into each well. The mixture is mixed gently and develop for 15 minutes in darkness. 100 ul/well of 2 M $H_2SO_4$ is added to quench the reaction and the reading at 450 nm is obtained.

The results of determination are provided as follows:

| Lot number Artemisia pollen skin prick-test fluid | ELISA value | | | | Positive control | Inhibitory ratio of sIgE |
|---|---|---|---|---|---|---|
| | 1 | 2 | 3 | mean | | |
| 30013511 | 0.37 | 0.32 | 0.28 | 0.32 | 0.85 | 62.3% |

The potency of allergen in *Artemisia* pollen skin prick-test fluid may be obtained according to the inhibitory ratio of sIgE. The higher the inhibitory ratio of sIgE, the higher the potency of allergen is.

EXAMPLE 11

Preparation of *Artemisia* Pollen Extract

1. *Artemisia* pollen is collected and air dried to constant weight;
2. The pollen is degreased by acetone for 5 times, until the acetone layer becomes colorless;
3. After the acetone is volatilized thoroughly, the pollen is grinded in a mortar manually for no less than 6 hours, then pulverized by high speed disperser (30,000 g, 30 times, 5 seconds for each time), and finally pulverized by ultrasonic wave (20 times, 5 seconds for each time), all of which are performed at 4° C.
4. To each gram of degreased pollen, 10 ml coca's buffer (5.0 g NaCl, 2.75 g $NaHCO_3$, 4 ml phenol, distilled water supplemented to 1000 ml) is added. The pollen is soaked in the buffer at 4° C. for 48 hour, during which the mixture is stirred for 6 times, 20 minutes for each time.
5. After leaching, the supernatant is obtained by centrifuge.
6. The leachate is dialysesd against physiological saline or PBS in a dialysis tube until the dialysate becomes colorless.
7. Positive pressure filtration is performed through 0.45 um filter, then the solution is dispensed and cryopreserved.
8. Total concentration of the protein in stock solution is determined by BCA method (in particularly, BCA protein assay kit (Pierce) is used).
9. Three batches of *Artemisia* pollen allergen extracts are prepared by above steps 1-8.
10. The concentration of protein in extracts is regulated by coca's buffer, so that three batches of extract have the same concentration of protein.

EXAMPLE 12

Use of *Artemisia* Pollen Standardized Serum Mixture in Determining Potency of *Artemisia* Pollen Extract 100 μl of *Artemisia* pollen allergen extract from 3 batches (Example 11) is mixed uniformly with *Artemisia* pollen standardized serum mixture (prepared by the method in Example 7 which is prepared from 500 serum samples) respectively at the same volume, with the *Artemisia* pollen standardized serum mixture used as control. All the mixtures are incubated in an incubator at 37° C. for one hour, then left in a refrigerator at 4° C. overnight (9-12 hours). The samples left at 4° C.

overnight then are transferred into a sterilized glass tube and the sIgE content is determined by Unicap100 Instrument. The relative content of sIgE for *Artemisia* pollen positive standardized serum is determined as 80.53. The results of determination upon mixing *Artemisia* pollen extract with standardized serum are provided as follows:

| Lot number of allergen preparation | Unicap value (KUA/L) | | | | Inhibitory ratio of sIgE |
|---|---|---|---|---|---|
| | 1 | 2 | 3 | mean | |
| 1 | 3.89 | 6.12 | 6.45 | 5.49 | 93.2% |
| 2 | 5.72 | 8.20 | 4.72 | 6.12 | 92.3% |
| 3 | 4.79 | 5.24 | 2.17 | 4.07 | 94.9% |

The potency of allergen in *Artemisia* pollen extract may be obtained according to the inhibitory ratio of sIgE. The higher the inhibitory ratio of sIgE, the higher the potency of allergen is.

EXAMPLE 13

Blending *Dermatophagoids farine* Positive Serum and Determining the Relative Content of sIgE Against *Dermatophagoids farine* Allergen in *Dermatophagoids farine* Positive Serum Mixture 1. Blending *Dermatophagoids farine* Positive Serum (1) Sera from patients diagnosed as having clinical symptoms of hypersensitivity disease to *Dermatophagoids farine* allergen are provided. The relative content of sIgE against *Dermatophagoids farine* allergen in said serum is determined according to the Unicap method in Example 2. 300 serum samples having the relative content of sIgE within 10-150 are selected. The mean of sIgE for 300 serum samples and deviation value of the relative content of sIgE in each serum with respect to said mean is calculated, 5% serum samples that have the largest and smallest deviation values are removed respectively, and the residual serum samples are mixed at the same volume. Three serum mixtures are prepared by the same method.

(2) Sera from patients diagnosed as having clinical symptoms of hypersensitivity disease to *Dermatophagoids farine* allergen are provided. The relative content of sIgE against *Dermatophagoids farine* allergen in said serum is determined by ELISA method in Example 2. 300 serum samples having the relative content of sIgE within 0.20-1.60 are selected. The mean of sIgE for 300 serum samples and deviation value of the relative content of sIgE in each serum with respect to said mean is calculated. 5% serum samples with the largest and smallest deviation value are removed respectively, and the residual serum samples are mixed at the same volume. Three serum mixtures are prepared by the same method.

2. Determining the relative content of sIgE against *Dermatophagoids farine* allergen in *Dermatophagoids farine* positive serum mixture as prepared (1) The content of sIgE in serum mixture is determined by Unicap method.

| | Serum mixture | | | | | | |
|---|---|---|---|---|---|---|---|
| | Serum mixture 1 prepared by Unicap method | Serum mixture 2 prepared by Unicap method | Serum mixture 3 prepared by Unicap method | Serum mixture 1 prepared by ELISA method | Serum mixture 2 prepared by ELISA method | Serum mixture 3 prepared by ELISA method | Sample standard deviation |
| The relative content of sIgE is determined by Unicap (KUA/L) | 78.99 | 80.24 | 85.63 | 81.78 | 86.33 | 87.26 | 3.479 |

(2) The content of sIgE in serum mixture is determined by ELISA method.

| | Serum mixture | | | | | | |
|---|---|---|---|---|---|---|---|
| | Serum mixture 1 prepared by Unicap method | Serum mixture 2 prepared by Unicap method | Serum mixture 3 prepared by Unicap method | Serum mixture 1 prepared by ELISA method | Serum mixture 2 prepared by ELISA method | Serum mixture 3 prepared by ELISA method | Sample standard deviation |
| The relative content of sIgE is determined by ELISA | 0.90 | 0.85 | 0.83 | 0.85 | 0.88 | 0.92 | 0.034 |

Conclusion may be drawn from the results of assay that in the case of obtaining 300 serum samples, the content of sIgE specific to *Dermatophagoids farine* in six *Dermatophagoids farine* positive serum mixtures prepared according to the two methods in this Example is stable. That is, if sIgE value in each serum mixture is determined by Unicap method, sample standard deviation is less than 3.90; if sIgE value in each serum mixture is determined by ELISA method, sample standard deviation is less than 0.040.

It may be known from the above examples that the content of sIgE in serum mixtures prepared according to the methods of the invention is stable. Therefore, it may be used as a reliable standard in the manufacture of allergen preparation and the quality control of allergen preparation can be ensured.

While the invention has been described with reference to specific embodiments thereof, it will be apparent to the skilled person in the art that various variations and modifications can be made therein without departing from the spirit and scope thereof. Therefore, all the variations and modifications should be included within the appended claims.

Though the present invention describes specific embodiments, it is apparent for the skilled person in the art to make various change and modification without departing from the spirit and scope of the present invention. The appended claims cover all these changes that are in the scope of the invention.

The invention claimed is:

1. A method for preparing a serum mixture which is used for determining potency of an allergen, wherein the method comprises the following steps:
   1) providing multiple serum samples from individuals moderately hypersensitive to said allergen;
   2) determining a relative content of an allergen specific IgE of each serum sample from said multiple serum samples, obtaining a mean value of the relative content of the allergen specific IgE of said multiple serum samples, and obtaining a deviation value of the relative content of the allergen specific IgE of the serum sample, the deviation value being calculated with the relative content of the serum sample and the mean value of said multiple serum samples; and
   3) removing at least 5% of said multiple serum samples that have the largest and smallest deviation values respectively, and mixing the residual serum samples at the same volume.

2. The method according to claim 1, wherein in said step 1), said moderately hypersensitive individuals have reactions of grade +++ when performing skin prick-test with said allergen.

3. The method according to claim 1, wherein said relative content of the allergen specific IgE in the serum sample is determined by CAP system or ELISA method.

4. The method according to claim 1, wherein in step 1), the number of said multiple serum samples is at least 300.

5. A serum mixture prepared by the method according to claim 1, wherein the allergen is *Dermatophagoids farine* or *Artemisia*, and a sample standard deviation of the allergen specific IgE value of the serum mixture is less than 3.90 KUA/L when determined by CAP system, or is less than 0.040 when determined by ELISA.

6. The use of A method of detecting allergen potency of an allergen using a serum mixture prepared by the method of claim 1 comprising the steps of:
   measuring a first concentration of free allergen specific IgE of the serum mixture;
   contacting the allergen with the serum mixture;
   measuring a second concentration of free allergen specific IgE of the serum mixture after the contacting; and
   comparing the first concentration and the second concentration.

7. The method of claim 6, wherein said allergen is in an allergen preparation used for detection, or is in an allergen preparation used for treatment.

8. A kit for detecting allergen potency, wherein said kit comprises the serum mixture of claim 5.

9. The method according to claim 1, wherein said allergen is selected from pollens, dust mites, foods, insects, fungi, cockroaches, and animal dander allergens.

10. The method according to claim 1, wherein in step 1) the number of said multiple serum samples is at least 500.

11. The method according to claim 1, wherein the allergen is *Dermatophagoids farine* or *Artemisia*, and the mean value of the relative content of the allergen specific IgE of said multiple serum samples is within the range of 75-85 KUA/L, and the deviation values of the residual serum samples are less than 30 KUA/L, when determined by CAP system.

12. The method according to claim 1, wherein the allergen is *Dermatophagoids farine* or *Artemisia*, and the mean value of the relative content of the allergen specific IgE of said multiple serum samples is within the range of 0.9-1.0, and the deviation values of the residual serum samples are less than 0.35, when determined by ELISA.

13. The kit of claim 8, wherein said allergen is in an allergen preparation used for detection, or is in an allergen preparation used for treatment.

* * * * *